United States Patent
Nabutovsky et al.

(10) Patent No.: US 9,763,591 B2
(45) Date of Patent: Sep. 19, 2017

(54) METHOD AND SYSTEM TO SUBDIVIDE A MAPPING AREA FOR MECHANICAL ACTIVATION ANALYSIS

(71) Applicant: Pacesetter, Inc., Sunnyvale, CA (US)

(72) Inventors: Yelena Nabutovsky, Mountain View, CA (US); Hoda Razavi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 35 days.

(21) Appl. No.: 14/703,749

(22) Filed: May 4, 2015

(65) Prior Publication Data
US 2015/0313555 A1 Nov. 5, 2015

Related U.S. Application Data

(60) Provisional application No. 61/988,767, filed on May 5, 2014.

(51) Int. Cl.
*A61B 5/0452* (2006.01)
*A61B 5/042* (2006.01)
(Continued)

(52) U.S. Cl.
CPC .......... *A61B 5/0422* (2013.01); *A61B 5/0006* (2013.01); *A61B 5/0022* (2013.01);
(Continued)

(58) Field of Classification Search
CPC ... A61B 5/7485; A61B 5/0006; A61B 5/0022; A61B 5/04012; A61B 5/042;
(Continued)

(56) References Cited

U.S. PATENT DOCUMENTS

| 5,391,199 A | 2/1995 | Ben-Haim |
| 5,713,367 A | 2/1998 | Arnold et al. |

(Continued)

FOREIGN PATENT DOCUMENTS

| EP | 1 070 480 A2 | 1/2001 |
| EP | 1 508 300 A1 | 2/2004 |

(Continued)

OTHER PUBLICATIONS

University of California, San Franscisco. "History of AF Ablation." https://cardiology.ucsf.edu/care/clinical/electro/ablation_hist.html Acessed on Jan. 17, 2017.*

(Continued)

*Primary Examiner* — Michael Carey
(74) *Attorney, Agent, or Firm* — Theresa A. Raymer

(57) ABSTRACT

A method and system are provided for subdividing a region of interest. The method and system utilize an intravascular mapping tool configured to be inserted into at least one of the endocardial or epicardial space. The mapping tool is maneuvered to select locations proximate to surfaces of the heart, while collecting map points at the select locations to form a point cloud data set during at least one cardiac cycle. The method and system further include selecting a region of interest from the point cloud data set, and forming a triangulation area that include a set of map points from the point cloud data set corresponding to the region of interest. Further, the method and system use a triangulation technique algorithm to generate at least one triangle within the triangulation area formed from at least a portion of the set of map points.

20 Claims, 12 Drawing Sheets

(51) Int. Cl.
*A61B 5/00* (2006.01)
*A61B 19/00* (2006.01)
*A61B 5/044* (2006.01)
*A61B 5/04* (2006.01)
*A61B 5/06* (2006.01)

(52) U.S. Cl.
CPC .......... *A61B 5/044* (2013.01); *A61B 5/04012* (2013.01); *A61B 5/061* (2013.01); *A61B 5/7485* (2013.01); *A61B 19/5244* (2013.01); *A61B 2019/5251* (2013.01); *A61B 2019/5265* (2013.01)

(58) Field of Classification Search
CPC ................ A61B 5/044; A61B 19/5244; A61B 2019/5265; A61B 2019/5251; A61B 5/0422; A61B 5/061; A61B 5/4785
USPC .......................... 600/508, 512, 515, 518, 527
See application file for complete search history.

(56) References Cited

U.S. PATENT DOCUMENTS

| | | |
|---|---|---|
| 6,233,476 B1 | 5/2001 | Strommer et al. |
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,397 B2 | 8/2007 | Hauck et al. |
| 7,276,064 B2 | 10/2007 | Paul et al. |
| 7,338,486 B2 | 3/2008 | Sliwa et al. |
| 7,386,339 B2 | 6/2008 | Strommer et al. |
| 7,505,809 B2 | 3/2009 | Strommer et al. |
| 7,697,973 B2 | 4/2010 | Strommer et al. |
| 7,881,769 B2 | 2/2011 | Sobe |
| 8,016,764 B1 | 9/2011 | Shelchuk |
| 8,195,292 B2 | 6/2012 | Noren et al. |
| 8,849,381 B2 | 9/2014 | Lux et al. |
| 9,162,067 B1 | 10/2015 | Farazi et al. |
| 2003/0093067 A1 | 5/2003 | Panescu |
| 2003/0233039 A1 | 12/2003 | Shao et al. |
| 2005/0154282 A1 | 7/2005 | Li et al. |
| 2006/0245536 A1 | 11/2006 | Boing |
| 2007/0055142 A1 | 3/2007 | Webler et al. |
| 2007/0073179 A1 | 3/2007 | Afonso et al. |
| 2007/0100332 A1 | 5/2007 | Paul et al. |
| 2007/0106146 A1 | 5/2007 | Altmann et al. |
| 2007/0181139 A1 | 8/2007 | Hauck |
| 2007/0244479 A1 | 10/2007 | Beatty et al. |
| 2007/0270705 A1* | 11/2007 | Starks ................. A61B 5/0402 600/523 |
| 2007/0299352 A1* | 12/2007 | Harlev ................. A61B 5/0422 600/509 |
| 2008/0009758 A1 | 1/2008 | Voth |
| 2008/0091193 A1 | 4/2008 | Kauphusman et al. |
| 2008/0190438 A1* | 8/2008 | Harlev ................. A61B 5/0536 128/898 |
| 2009/0163904 A1 | 6/2009 | Miller et al. |
| 2009/0171345 A1 | 7/2009 | Miller et al. |
| 2009/0275828 A1 | 11/2009 | Shachar et al. |
| 2010/0168550 A1 | 7/2010 | Byrd et al. |
| 2010/0268059 A1 | 10/2010 | Ryu |
| 2011/0190593 A1 | 8/2011 | McNair et al. |
| 2011/0208038 A1 | 8/2011 | Konofagou et al. |
| 2011/0243401 A1 | 10/2011 | Zabair et al. |
| 2012/0184863 A1 | 7/2012 | Harlev et al. |
| 2013/0222415 A1 | 8/2013 | Vilsmeier |
| 2013/0272592 A1 | 10/2013 | Eichler et al. |
| 2015/0045867 A1 | 2/2015 | Krishnan et al. |
| 2015/0133802 A1 | 5/2015 | Nabutovsky et al. |
| 2015/0141765 A1 | 5/2015 | Razavi et al. |
| 2015/0141858 A1 | 5/2015 | Razavi et al. |
| 2017/0042481 A1* | 2/2017 | Olson .................. A61B 5/6852 |

FOREIGN PATENT DOCUMENTS

| | | |
|---|---|---|
| EP | 2 757 528 A1 | 7/2014 |
| WO | 97/24981 | 7/1997 |
| WO | 2012/090148 A1 | 7/2012 |

OTHER PUBLICATIONS

Non-Final Office Action mailed Dec. 11, 2015; Related U.S. Appl. No. 14/703,460.
Non-Final Office Action mailed Sep. 30, 2015; Related U.S. Appl. No. 14/270,181.
Notice of Allowance mailed Dec. 8, 2015; Related U.S. Appl. No. 12/347,216.
Final Office Action mailed Jan. 22, 2016; Related U.S. Appl. No. 14/240,176.
Non-Final Office Action mailed Feb. 8, 2016; Related U.S. Appl. No. 14/270,181.
Notice of Allowance mailed Jun. 22, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action mailed Aug. 10, 2015; Related U.S. Appl. No. 12/347,216.
Amendment filed Jun. 25, 2015; Related U.S. Appl. No. 12/347,216.
Final Office Action mailed May 4, 2015; Related U.S. Appl. No. 12/347,216.
Amendment filed Dec. 18, 2014; Related U.S. Appl. No. 12/347,216.
Non-Final Office Action mailed Oct. 2, 2014; Related U.S. Appl. No. 12/347,216.
Advisory Action mailed May 1, 2014; Related U.S. Appl. No. 12/347,216.
Amendment filed Apr. 24, 2014; Related U.S. Appl. No. 12/347,216.
Applicant Interview Summary, Apr. 21, 2014; Related U.S. Appl. No. 12/347,216.
Final Office Action mailed Feb. 25, 2014; Related U.S. Appl. No. 12/347,216.
Amendment filed Feb. 4, 2014; Related U.S. Appl. No. 12/347,216.
Non-Final Office Action mailed Nov. 21, 2013; Related U.S. Appl. No. 12/347,216.
Amendment filed Oct. 29, 2012; Related U.S. Appl. No. 12/347,216.
Advisory Action mailed Oct. 11, 2012; Related U.S. Appl. No. 12/347,216.
Amendment filed Oct. 1, 2012; Related U.S. Appl. No. 12/347,216.
Advisory Action mailed Sep. 12, 2012; Related U.S. Appl. No. 12/347,216.
Amendment filed Aug. 28, 2012; Related U.S. Appl. No. 12/347,216.
Final Office Action mailed Jun. 29, 2012; Related U.S. Appl. No. 12/347,216.
Amendment filed May 14, 2012; Related U.S. Appl. No. 12/347,216.

(56) References Cited

OTHER PUBLICATIONS

Interview Summary, Feb. 28, 2012; Related U.S. Appl. No. 12/347,216.
Non-Final Office Action mailed Feb. 13, 2012; Related U.S. Appl. No. 12/347,216.
Notice of Allowance mailed Oct. 27, 2015; Related U.S. Appl. No. 14/328,523.
Notice of Allowance mailed Feb. 25, 2016; Related U.S. Appl. No. 14/328,513.
Notice of Allowance mailed Feb. 25, 2016; Related U.S. Appl. No. 14/703,760.
Notice of Allowance mailed Apr. 19, 2016; Related U.S. Appl. No. 14/270,181.
USPTO, "Notice of Allowance for U.S. Appl. No. 14/270,176", mailed May 20, 2016.
USPTO, "Non-Final Office Action for U.S. Appl. No. 14/703,735". Date mailed Jan. 12, 2017.
USPTO, "Non-Final Office Action for U.S. Appl. No. 14/703,744", Date Mailed Jan. 13, 2017.
USPTO, "Non-Final Office Action for U.S. Appl. No. 14/270,186", Date mailed Feb. 27, 2017.
USPTO, "Non-Final Office Action for U.S. Appl. No. 14/478,707", Date mailed Mar. 2, 2017.
USPTO, "Non-Final Office Action for U.S. Appl. No. 14/703,757", Date mailed Apr. 6, 2017.

* cited by examiner

METHOD AND SYSTEM TO SUBDIVIDE A MAPPING AREA FOR MECHANICAL ACTIVATION ANALYSIS

RELATED APPLICATION DATA

This present application relates to and claims priority from the following application: U.S. provisional application Ser. No. 61/988,767, filed May 5, 2014, titled "Method and System to Subdivide a Mapping Area for Mechanical Activation Analysis", which is expressly incorporated herein by reference in its entirety in the present application.

BACKGROUND OF THE INVENTION

Embodiments of the present disclosure generally relate to methods and systems for cardiovascular navigation, and more particularly for calculating the strain from characterization data of a cardiac chamber or organ.

Cardiovascular navigation systems (CNS) provide real-time position and orientation information in relation to a part of the cardiovascular system, such as, the heart based on sensors placed at various locations within the cardiovascular system. The CNS may be integrated with a fluoroscopic (or other diagnostic) imaging system and track the sensors continuously within an imaging volume defined by the fluoroscopic system, on both live and recorded background diagnostic images.

Recently, it has been proposed to utilize the CNS to evaluate the motion of the heart and identify a desired (e.g., optimal) location for placement of a left ventricular (LV) lead. For example, the CNS may systematically record information, such as displacement of the sensors, associated with various endocardial and epicardial locations of the LV. Epicardial locations may include mapping within the coronary sinus branches as well as mapping directly on the epicardial surface of the LV via a sub-xiphoid puncture technique, for example. Depending on the size of the heart and other factors during the procedure, there may be between 40 and 120 endocardial LV locations and up to 10 epicardial locations at which the MDG system obtains recordings for each patient.

Systems have been proposed to characterize the motion of the heart, specifically on the qualitative techniques of characterizing motion. However, the systems proposed thus far do not offer sufficient information to prepare acquired characterization data for strain analysis. A need remains for methods and system that can offer more information about preparing characterization data for strain analysis.

SUMMARY

In accordance with an embodiment herein, a method is provided for subdividing a region of interest. The method includes utilizing an intravascular mapping tool configured to be inserted into at least one of the endocardial or epicardial space. The mapping tool maneuvered to select locations proximate to surfaces of the heart, while collecting map points at the select locations to form a point cloud data set during at least one cardiac cycle. The method further includes selecting a region of interest from the point cloud data set, and forming a triangulation area that includes a set of map points from the point cloud data set. The set of map points includes at least map points within the region of interest. Further, the method uses a triangulation technique algorithm to generate at least one triangle within the triangulation area formed from at least a portion of the set of map points.

DETAILED DESCRIPTION

Figure 1:
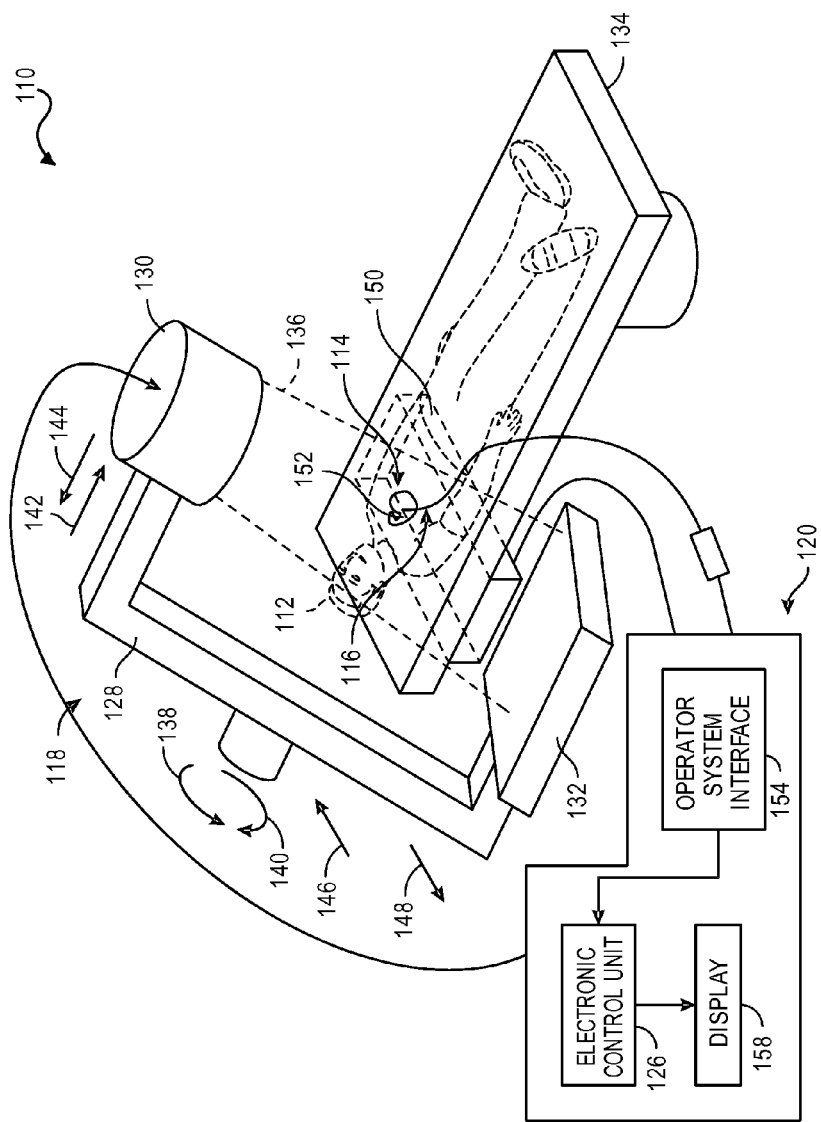
FIG. 1 illustrates a cardiovascular navigation system for use in imaging an anatomical region of the heart and to collect motion data, in accordance an embodiment herein.

Embodiments herein may be implemented with, and/or utilize aspects of, the methods and system described in the following applications:

U.S. patent application Ser. No. 14/328,523, filed Jul. 10, 2014, titled "METHOD AND SYSTEM TO ASSESS MECHANICAL DYSSYNCHRONY BASED ON MOTION DATA COLLECTED BY A NAVIGATION SYSTEM", U.S. patent application Ser. No. 14/328,513, filed Jul. 10, 2014, titled "METHOD AND SYSTEM TO MEASURE CARDIAC MOTION USING A CARDIOVASCULAR NAVIGATION SYSTEM", U.S. patent application Ser. No. 14/478,707, filed Sep. 5, 2014, titled "METHOD AND SYSTEM TO IDENTIFY MOTION DATA ASSOCIATED WITH CONSISTENT ELECTRICAL AND MECHANICAL BEHAVIOR FOR A REGION OF INTEREST", U.S. patent application 61/988,779, filed May 5, 2014, titled "METHODS AND SYSTEMS TO CALCULATE TIME OF MECHANICAL ACTIVATION USING CHARACTERIZATION MOTION DATA AREA STRAINS", U.S. patent application Ser. No. 14/270,181, filed May 5, 2014, titled "METHOD AND SYSTEM TO CHARACTERIZE MOTION DATA BASED ON NEIGHBORING MAP POINTS", U.S. patent application Ser. No. 14/270,186, filed May 5, 2014, titled "METHOD AND SYSTEM FOR CACLULATING STRAIN FROM CHARACTERIZATION DATA OF A CARDIAC CHAMBER", U.S. patent application Ser. No. 14/270,176, filed May 5, 2014, titled "METHOD AND SYSTEM FOR DISPLAYING A THREE DIMENSIONAL VISUALIZATION OF CARDIAC MOTION", U.S. patent application 61/988,735, filed May 5, 2014, titled "METHOD AND SYSTEM TO DETERMINE CARDIAC CYCLE LENGTH IN CONNECTION WITH CARDIAC MAPPING", U.S. patent application 61/988,763, filed May 5, 2014, titled "METHOD AND SYSTEM TO EQUALIZING CARDIAC CYCLE LENGTH BETWEEN MAP POINTS", U.S. patent application 61/988,771, filed May 5, 2014, titled "CARDIAC RESYNCHRONIZATION SYSTEM AND METHOD", and U.S. patent application 61/988,774, filed May 5, 2014, titled "SYSTEM AND METHOD FOR EVALUATING LEAD STABILITY OF AN IMPLANTABLE MEDICAL DEVICE".

All of the above cited applications are expressly incorporated herein by reference in their entirety.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates a cardiovascular navigation system (CNS) 110, of an embodiment, for use in imaging an anatomical region of a patient 112, such as, a heart 114. A medical tool 116 is placed within the anatomical region, such as for example, an electrophysiological (EP) mapping catheter (e.g., a guide wire), or a catheter generally described or shown in U.S. Pat. No. 7,881,769, which is expressly incorporated herein by reference. The medical tool 116 includes a plurality of electrophysiological sensors 152 that may be placed on the endocardial or epicardial surface of the left ventricle (LV) of the heart 114. The electrophysiological sensors 152 may be attached to the distal or proximal end of the medical tool 116, or any point in between. The electrophysiological sensors 152 measure a position and an electrical potential or an electric current of biological cells and tissues. The electrophysiological sensors 152 transmits the position and electrical potential information to an electronic control unit (ECU) 126. For example, the electrophysiological sensors 152 may be positioned by the medical tool 116 to measure point specific (PS) motion data for a plurality of map points of the wall of the heart 114. It should be understood, however, that the electrophysiological sensors 152 could be used in a variety of anatomical regions or alternative map points within the heart 114 or other organs in which motion characterization may be of interest. Additionally or alternatively, the electrophysiological sensors 152 may be replaced by separate motion sensors and electrical sensors. The motion sensors in contact with the region of interest (e.g., the LV of the heart 114) measuring the position sensors as well as the electrical sensors that are measuring the PS motion data of the region of interest. Optionally, the ECU 126 may receive the PS motion data and electrical sensor measurements simultaneously from the motion sensors and electrical sensors.

A navigation system 120 is provided to determine the position and orientation of the medical tool 116 within the body of the patient 112. In the illustrated embodiment, the navigation system 120 comprises a magnetic navigation system in which magnetic fields are generated in the anatomical region and position sensors associated with the medical tool 116 generate an output that is responsive to the position of the sensors within the magnetic field. The navigation system 120 may comprise, for example, the systems generally shown and described in, for example, U.S. Pat. Nos. 6,233,476, 7,197,354, 7,386,339, and 7,505,809 all of which are expressly incorporated by reference in their entirety. Although a magnetic navigation system is shown in the illustrated embodiment, it should be understood that the embodiments could find use with a variety of navigation systems including those based on the creation and detection of axes specific electric fields. The navigation system 120 may include a transmitter assembly 150.

The transmitter assembly 150 may include a plurality of coils arranged orthogonally to one another to produce a magnetic field in and/or around the anatomical region of interest. It should be noted that, although the transmitter assembly 150 is shown under the body of the patient 112 and under the table 134 in FIG. 1, the transmitter assembly 150 may be placed in another location, such as, attached to the radiation emitter 130, from which the magnetic field generators can project a magnetic field in the anatomical region of interest. In accordance with certain embodiments the transmitter assembly 150 is within the field of view 136. The ECU 126 may control the generation of magnetic fields by transmitter assembly 150.

The electrophysiological sensors 152 are configured to generate an output dependent on the relative position of electrophysiological sensors 152 within the field generated by the transmitter assembly 150. In FIG. 1, the electrophysiological sensor 152 and the medical tool 116 are shown disposed around the heart 114. The navigation system 120 determines the location of the electrophysiological sensors 152 within the generated field, and thus the position of the medical tool 116 as well. The navigation system 120 may further determine navigation coordinates, such as a cartesian coordinate (e.g., (X, Y, Z)), of the navigation coordinate system.

The ECU 126 of the navigation system 120 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 126 may receive a plurality of input signals including signals generated by the medical tool 116, the electrophysiological sensors 152, an operator system interface 154 (e.g., keyboard, touchscreen, or the like), and one or more patient reference sensors (not shown) and generate a plurality of output signals including those used to control the medical tool 116 and/or the display 158. The ECU 126 may also receive an input signal from an organ monitor (not shown), such as an ECG monitor, and sort or segregate images from an imaging system 118 based on a timing signal of a monitored organ. For example, ECU 126 may sort images based on the phase of the patient's cardiac cycle at which each image was collected, as more fully described in U.S. Pat. No. 7,697,973, which is hereby incorporated by reference in its entirety.

Optionally, the CNS 110 may include an imaging system 118. The CNS 110 may further include a registration system for registering a group of images of the anatomical region of the patient 112 in a navigation coordinate system of the navigation system 120 as generally described and shown in U.S. Patent Publication 2013/0272592 and International Pub. No. WO 2012090148, the entire disclosure of which is expressly incorporated herein by reference.

The imaging system 118 may be provided to acquire images of the heart 114 or another anatomical region of interest. The imaging system 110 may, for example, comprise of a fluoroscopic imaging system. Additionally or alternatively, rather than a fluoroscopic imaging system, computed tomography (CT) imaging systems, a three-dimensional radio angiography (3DRA) system, SPECT, PET, X-ray, MR, ultrasound and the like may be used. Although the imaging system 118 is described herein for an exemplary embodiment of the invention, the imaging system 118 is not required for the inventive subject matter described within this application.

The imaging system 118 may include a C-arm support structure 128, a radiation emitter 130, and a radiation detector 132. The emitter 130 and detector 132 are disposed on opposite ends of the support structure 128 and disposed on opposite sides of the patient 112 as the patient 112 lays on an operation table 134. The emitter 130 and detector 132 define a field of view 136 and are positioned such that the field of view 136 includes the anatomical region of interest as the patient 112 lays on the operation table 134. The imaging system 118 is configured to capture images of anatomical features and other objects within the field of view 136. The support structure 128 may have freedom to rotate about the patient 112 as shown by lines 138 and 140. The support structure 128 may also have freedom to slide along lines 142 and 144 (e.g., along the cranio-caudal axis of the patient 112) and/or along lines 146 and 148 (e.g., perpendicular to the cranio-caudal axis of the patient 112). Rotational and translational movement of the support structure 128 yields corresponding rotational and translational movement of the field of view 136. Additionally or alternatively, the navigation system 120 may adjust the navigation coordinates of the position of the medical tool 116 to compensate for changes in the C-arm support structure 128 and respiratory movements of the patient as disclosed in the U.S. application Ser. No. 14/328,513, entitled, "METHOD TO MEASURE CARDIAC MOTION USING A CARDIO-VASCULAR NAVIGATION SYSTEM," which is expressly incorporated herein by reference in its entirety.

The imaging system 118 may acquire a group of images of an anatomical region of the patient 112 by first shifting along lines 142, 144, 146, and/or 148 to place the anatomical region of interest within the field of view 136. Second, the support structure 128 may rotate the radiation emitter 130 and the radiation detector 132 about the patient 112, keeping the anatomical region within the field of view 136. The imaging system 118 may capture images of the anatomical region as the support structure 128 rotates, providing a group of two-dimensional images of the anatomical region from a variety of angles. The group of images may be communicated to the ECU 126 for image processing and display. The group of images may comprise a sequence of images taken over a predetermined time period.

Additionally, one or more patient reference sensors (not shown) may be on the body of the patient 112, for example, on the chest. The patient reference sensors measure a displacement and orientation of the patient reference sensors relative to a predetermined reference point, such as, the electrophysiological sensors 152 or the transmitter assembly 150.

Figure 2:
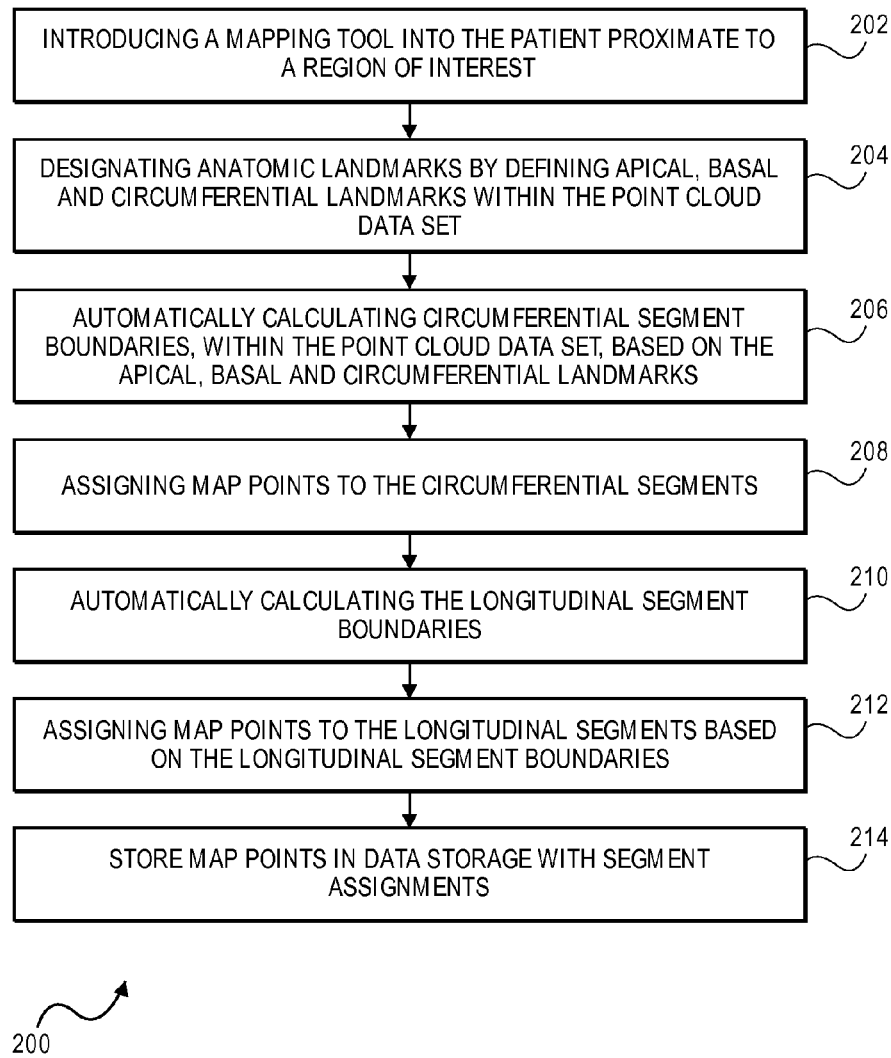
FIG. 2 illustrates a method performed in accordance with embodiments herein for assigning map points to anatomical segments of the heart.

FIG. 2 illustrates a method 200 performed in accordance with embodiments herein for assigning map points to anatomical segments of the heart. Throughout the present application, examples are provided in connection with mapping the left ventricle (LV). It should be recognized that the operations described herein may be used to map other regions of the heart. When mapping other regions of interest in the heart, different reference points and landmarks may be used.

Beginning at 202, a mapping tool (e.g., the medical tool 116) is introduced into the patient 112 proximate to a region of interest (e.g., the LV). Images are displayed to the user through the display 158. The images may be collected from various diagnostic imaging modalities (e.g. fluoroscopy, X-ray, MR, ultrasound, CT, PET, SPECT and the like) from the imaging system 118. Information from the navigation system 120, regarding the mapping tool, is combined with the images of the region of interest, and graphical representations are displayed of the mapping tool, in combination with the diagnostic image(s) on the display 158. For example, the mapping tool may be displayed superimposed upon the diagnostic image(s). By way of example, the physician may utilize an intravascular mapping tool that is configured to be inserted proximate to the heart, endocardially and/or epicardially. The physician maneuvers the mapping tool between multiple locations of interest that are proximate to select areas on interior and/or exterior surfaces of the heart. For example, the physician may manipulate a mapping tool within the left ventricle and/or right ventricle to collect endocardial mapping data associated with interior surfaces of the chambers of the heart.

Additionally or alternatively, the physician may maneuver the mapping tool along one or more veins that extend about an exterior of a select region/chamber of the heart, such as the right ventricle and/or left ventricle, to collect epicardial mapping data. The medical tool 302 may acquire point specific (PS) motion data of the heart at numerous map points positioned along the walls of the various chambers during at least one cardiac cycle.

Figure 3:
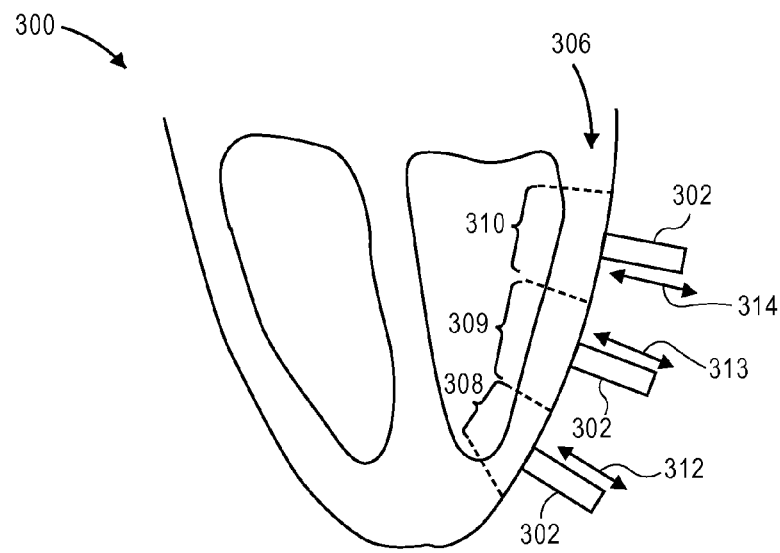
FIG. 3 illustrates a graphical representation of a plurality of map points of a heart.

FIG. 3 illustrates a graphical representation of a portion of a heart 300 with a medical tool 302 positioned to acquire PS motion data. For example, the medical tool 302 may be used to acquire PS motion data for a plurality of map points 308-310 associated with a heart wall 306. The PS motion data forms a portion of a point cloud data set. The point cloud data set may include all data collected by the medical tool 302, which may include information other than PS motion data. The term "point specific" is used to indicate that the motion data is associated with a single select location on the heart wall. The data values represent positions of the single select location over one or more cardiac cycles. The example of FIG. 3 shows three map points of interest 308-310 along the heart wall. Optionally, more or fewer map points of interest may be designated to expand the point cloud data set. The medical tool 302 (which may correspond to the medical tool 116 of FIG. 1 with the plurality of electrophysiology sensors 152) is positioned directly against the heart wall 306 at one or more points of interest 308-310. The tool 302 measures movement of the one or more points over a select period of time. In the example of FIG. 3, the tool 302 is shown positioned against map points 308-310 at different points in time.

For example, the tool 302 is positioned, during a first measuring operation, at the map point 308 while collecting PS motion data associated with movement (e.g., along the arrow 312) by the map point 308. The movement may be in various linear, transverse, or rotational directions. The map point data is continuously or periodically collected and added to data collection, generally referred to as the point cloud data set. Next, the tool 302 may be positioned, during a second measuring operation, at the map point 309 while collecting PS motion data associated with movement (e.g., along the arrow 313) by the map point 309. Next, the tool 302 is positioned, during a third measuring operation, at the map point 310 while collecting PS motion data associated with movement (e.g., along the arrow 314) by the map point 310. The position of the tool 302 may be continuously monitored by a navigation system (e.g., the navigation system 120) to obtain sets of PS motion data associated with each map point 308-310 over a select period of time, such as, during at least one cardiac cycle.

The point cloud data set expands over time thereby increasing an amount of information regarding the electrical and/or mechanical behavior of the region of interest within the heart. The point cloud data set is stored in a data storage (e.g., such as at a local terminal or workstation, a local area network, a wide area network, on a network, or at a remote data storage facility). By way of example, the data storage may be configured to store map point data collected by an intravascular mapping tool configured to be inserted into at least one of the endocardial or epicardial space. The mapping tool is maneuvered to select locations proximate to surfaces of the heart, while collecting the map point data at map points to form a point cloud data set during at least one cardiac cycle, the map point data represents at least one of motion or electrical activity data at the map points.

As explained herein, various analyses may be performed iteratively upon the point cloud data set throughout the data collection process. It is not necessary for a complete point cloud to be collected before analyzing the map point data.

Optionally, the navigation system 120 (FIG. 1) may perform pre-processing on the point cloud data set. For example, the CNS 110 may filter or remove PS motion data within the point cloud data set that was acquired during irregular or invalid beats (e.g., ectopic beats). The navigation system 120 may receive electrical sensor measurements of the patient 112 from a 12-lead surface electrocardiogram (ECG), body surface mapping (BSM), subcutaneous ECG, a uni- or bi-polar intracardiac electrograms (IEGMs) of a catheter, such as the medical tool 116, placed in the coronary sinus (CS), right ventricular (RV apex), or the like. The navigation system 120 may identify the invalid or irregular beats from the electrical sensor measurements and remove the invalid or irregular beats with the corresponding PS motion data subset acquired during the beat from the point cloud data set as disclosed in U.S. application Ser. No. 14/478,707.

Optionally, the navigation system 120 may adjust PS motion data within the point cloud data set based on motion waveforms. A motion waveform represents motion of a map point during a cardiac cycle as defined by the PS motion data. For example, the PS motion data may be adjusted temporally equalized by "stretching" motion waveforms that have shorter cycle lengths until the shorter motion waveform subsets have a length equal to a predetermined or common time interval. The common time interval may be predetermined, or automatically selected, such as by choosing a length corresponding to the longest, shortest, or average length of the motion waveforms define by the PS motion data within the point cloud data set. The time interval may be set to begin at a point in time defined by a global signal such as the peak of the R-wave as detected by using the Electrocardiogram (ECG) or Intracardiac Electrogram (IEGM) signals as disclosed in the U.S. Provisional Application No. 61/910,600. Optionally, the time interval may be defined to begin based on another global marker of electrical activity (e.g., the T-wave, P-wave).

Additionally or alternatively, the navigation system 120 may apply a rotation technique to the motion waveform to correct for non-periodicity, such as the rotation techniques described in U.S. application Ser. No. 14/328,513. A periodic motion waveform of a map point during the cardiac cycle has, at the beginning and end of the cardiac cycle, approximately the same measured displacement or position. Non-periodicity may occur from errors in the acquired PS motion data for the map point that defines the motion waveform. For example, if the electrophysiological sensor 152 is not maintained directly against the heart wall during the entire cardiac cycle the PS motion data may drift.

Figure 4:
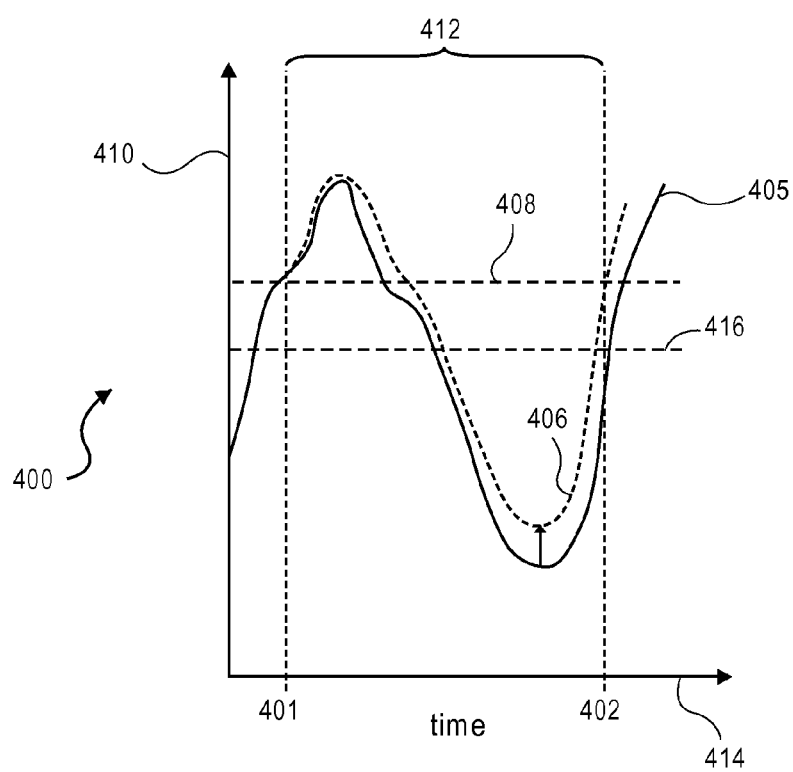
FIG. 4 illustrates a motion waveform associated with a map point being rotated in accordance with an embodiment herein.

FIG. 4 illustrates a graph 400 for a motion waveform 405 that is defined by a plurality of PS motion data associated with a select map point (e.g., the map point 308 in FIG. 3). The motion waveform 405 represents a displacement of the map point with respect to a vertical axis 410 over time as denoted along a horizontal axis 414. A cardiac cycle 412 is represented between start 401 and end 402. At the start 401 of the cardiac cycle 412, the motion waveform 405 has a first measured displacement as shown by horizontal dashed line 408. At the end 402 of the cardiac cycle 412, the motion waveform 405 has a second measured displacement as shown by horizontal dashed line 416. The difference in the displacements (relative to the vertical axis 410) of the motion waveform 405 at the start 401 and the end 402 of the cardiac cycle 412 indicates that the motion waveform 405 is non-periodic. A rotation technique may be applied to generate a rotated motion waveform 406 that is periodic such as disclosed in U.S. application Ser. No. 14/328,513.

The rotation technique shifts the PS motion data from the motion waveform 405 until defining the rotated motion waveform 406. The rotated motion waveform 406 has a common measured displacement at the start 401 and end 402 of the cardiac cycle 412. The common measured displacement corresponds to dashed line 408.

Additionally or alternatively, the navigation system 120 may average the PS motion data that corresponds to a map point (e.g., the map point 308) measured over a plurality of cardiac cycles to determine an average motion waveform for the map point. For example, the motion waveform may be combined through averaging or otherwise. Optionally, the PS motion data, which is utilized in connection with embodiments described hereafter, may include information indicative of a radial component of wall movement, and/or may include information indicative of a longitudinal component of wall movement. Optionally, the PS motion data may include information associated with 3-dimensional (3-D) movement calculated as a 3-D distance from an initial position at a select starting point in the cardiac cycle, such as an R-wave or local electrical activation time.

Returning to FIG. 2, at 204, the method designates anatomic landmarks by defining apical, basal, and circumferential landmarks within the point cloud data set. The anatomical landmarks may be designated through manual operations by the user. Additionally or alternatively, the anatomical landmarks may be designated through automatic calculations based on analysis of the point cloud data set, for example, as described in U.S. patent application Ser. No. 14/270,191, titled "METHOD AND SYSTEM TO AUTOMATICALLY ASSIGN MAP POINTS TO ANATOMICAL SEGMENTS". The landmarks are located at various locations based upon the shape and nature of the region of interest. For example, at least one landmark is located proximate to, or at, the apex of the region of interest. Another landmark is located at, or proximate to, a middle of a base of the region of interest, while another landmark is located circumferentially from the base at an outer limit of the region of interest. For example, when the region of interest represents the right or left ventricle, the apex landmark represents the apex of the RV or LV. The basal landmark represents the base of the RV or LV and the circumferential landmark represents the left or right ventricular outflow tract.

One or more axes may be defined from the landmarks. For example, a long axis of the RV or LV is defined as a line connecting the apex to the basal point/landmark. A circumferential line is drawn from the basal landmark to the circumferential landmark. The long axis and circumferential line are used to position and orient a transformation coordinate system. For example, the long axis may be used as a Z-axis and the circumferential line is used as the circumferential line of the cylindrical coordinate system. The long axis and circumferential line are used as a basis to convert the point data from a base coordinate system, such as the Cartesian coordinate system, to a coordinate system associated with the regions of interest. For example, location coordinates for point data may be converted from XYZ Cartesian coordinates to longitudinal, radial and circumferential coordinates of the cylindrical coordinates.

At 206, the method 200 automatically calculates circumferential segment boundaries, within the point cloud data set, based on the apical, basal and circumferential landmarks.

At 208, the method 200 segments the region of interest (ROI) into at least one segment that includes a corresponding set of map points from the point cloud data set. To segment the ROI, the method assigns map points to the circumferential segments as defined at 206. In order to automatically assign each map point, the method determines a corresponding segment of the anatomical map. To do so, in at least one embodiment, the method defines a reference line between the basal landmark and circumferential landmark. The circumferential location of each map point (θm) at a predefined point in the cardiac cycle, such as at the peak of the QRS complex, is compared against the circumferential landmark (θLVOT). A tolerance may be used such as (θLVOT−π/6−tolerance)<θm≤(θLVOT+π/6+tolerance).

Each map point is assigned to the corresponding wall segment, where the circumferential landmark is used to identify a reference wall segment, such as the anteroseptal wall segment. Upon definition of the segment boundaries of the first wall segment, with the option of including a circumferential tolerance, the definitions of the other wall segments include the subsequent addition or subtraction of multiples of tolerances (e.g., π/3+tolerance) until the entire circumference of a region of interest (e.g, LV) is assigned to the appropriate wall segment.

Additionally or alternatively, the navigation system 120 may convert the map points from Cartesian coordinates to a cylindrical coordinate system (e.g., r, θ, Z) when assigning the map points. Various techniques may be used for transforming between the Cartesian and cylindrical coordinate systems. Alternative base coordinate systems may be used instead of the Cartesian coordinate system. Optionally, the map points may be converted to an alternative coordinate system other than the cylindrical coordinate system. For example, the map points may be transformed to the spherical, polar or another system.

At 210, the method calculates the longitudinal segment boundaries. At 212, the method assigns map points to the segments based on the longitudinal segment boundaries. For example, the method performs segmentation along the long axis for definition of apical vs. mid-ventricular vs. basal points. The longest available length of the long axis ($L_{Long\ Axis}$) is determined. An apical portion (AP) parameter is then defined which determines the extent of the apical segments and $L_{Long\ Axis}$ is divided by AP, such that any point with a longitudinal coordinate less than $L_{Long\ Axis}$/AP is assigned to the apex. A typical value for AP may be 3, in which the apical segments cover ⅓ of the length of the entire wall from apex to base. Next, the remaining points with longitudinal coordinates less than $$\frac{L_{LongAxis}(AP+1)}{2AP}$$

are assigned to the mid-ventricular segments and those with longitudinal coordinates more than this value are assigned to the basal segments. A longitudinal tolerance can also be introduced to allow for some flexibility in this assignment.

At 214, the map points are stored in a data storage with associated segment assignments. Additionally or alternatively, the navigation system 120 may calculate circumferential and longitudinal segment boundaries, for the point cloud data set, based on the apical, basal and circumferential landmarks as disclosed in U.S. application Ser. No. 14/270, 191, filed on May 5, 2014, titled "METHOD AND SYSTEM TO AUTOMATICALLY ASSIGN MAP POINTS TO ANATOMICAL SEGMENTS".

Figure 5:
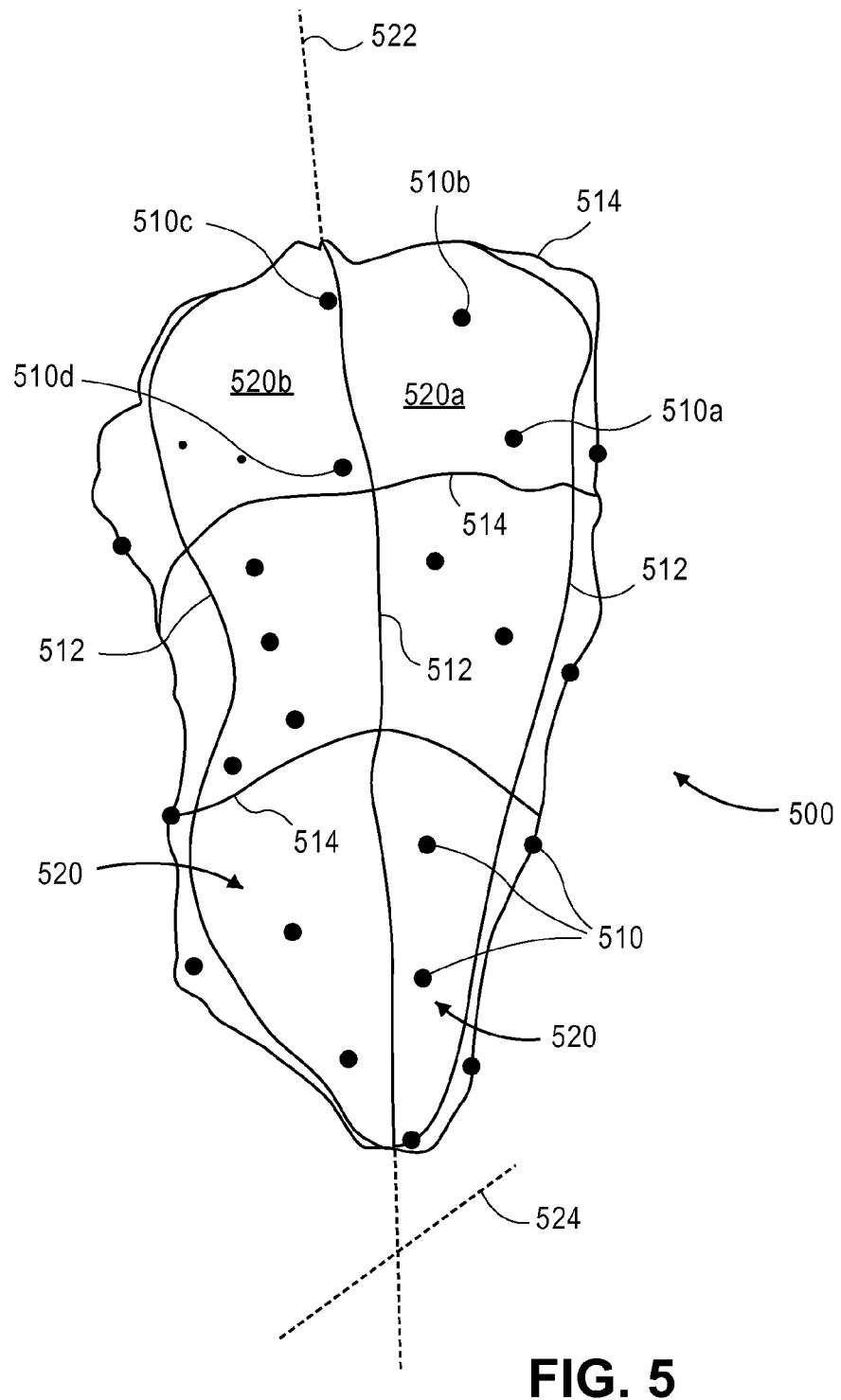
FIG. 5 illustrates map points within a longitudinal segmented left ventricalar in accordance with an embodiment herein.

FIG. 5 illustrates a three dimensional (3D) visualization 500 of map points 510 located along the LV. The visualization 500 may be displayed on the display 158 in FIG. 1. FIG. 5 illustrates the left ventricular of the heart divided into segments 520 (not all segments shown) by circumferential segment boundaries 512 and longitudinally segment boundaries 514 (not all boundaries shown). It should be noted in alternative embodiments the number of circumferential and longitudinal segments may be fewer than or greater than shown in FIG. 5. Optionally, the three dimensional visualization 500 may include a graphical marker for an apical landmark, a basal landmark, and circumferential landmarks (e.g., septal, anterior-septal, anterior). The map points 510 are assigned to the segments in accordance with the operations at 208 and 210. In particular, as one example, the map points 510 are assigned to an associated segment 520a based on the location of the map points 510*a-b*, while the map points 510*c-d* are assigned to the segment 520*b*.

Additionally or alternatively, the map points (as described above) may be based on a cylindrical coordinate system. For example, the map points may be oriented based on a longitudinal axis 522, a polar or radial axis 524 with an origin approximate to the apex, and an angular coordinate or azimuth from the radial axis 524. It should be noted, in alternative embodiments the coordinate system may be oriented or have an origin on other landmarks within the region of interest, for example, the base, septal, or the like. Optionally, the coordinate system may be oriented or have an origin external to the region of interest (e.g., the heart), for example based on a reference external to the patient such as the transmitter assembly 150 of the CNS 110.

Optionally, a subset of the map points may be assigned to multiple segments based on the distance of the map points from at least one of the longitudinal and/or circumferential segment boundaries 512 and 514. For example, the map point 510*d* may be associated with both the segments 520*a-b* based on the proximity to the circumferential segment boundary 512.

Figure 6:
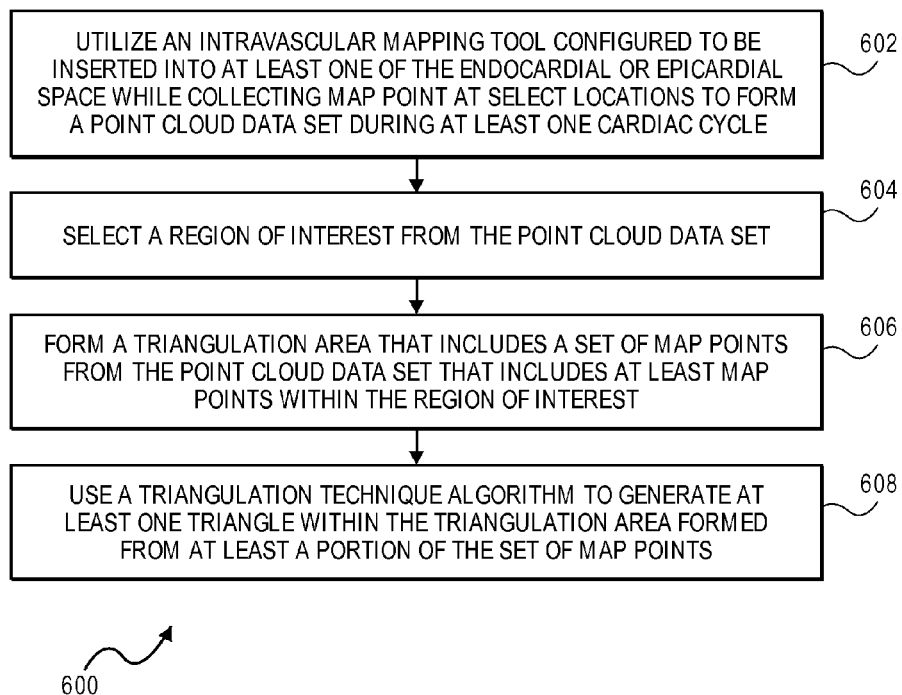
FIG. 6 illustrates a flow chart for sub-dividing a region of interest.

FIG. 6 illustrates a flowchart for subdividing a region of interest (e.g., 520) into geometric areas (e.g., triangles or triangular areas) for further analysis, such as, to determine strain. The method 600, for example, may employ structures or aspects of various embodiments (e.g., systems and/or methods) discussed herein (e.g., the CNS 110 in FIG. 1). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It should be noted that, other methods may be used, in accordance with an embodiment herein.

At 602, the method 600 utilizes an intravascular mapping tool configured to be inserted into at least one of the endocardial or epicardial space while collecting map points at select locations to form a point cloud data set during at least one cardiac cycle as explained in connection with FIG. 3.

At 604, the method 600 selects a region of interest from the point cloud data set. For example, the navigation system 120 may automatically, or the clinician via the operator system interface 154 may manually select a region of interest for further analysis in accordance with embodiments herein. By way of example, the user may use a mouse, cursor, and/or keyboard of the system interface 154 to "click on", draw around, or otherwise designate the region of interest. The region of interest may be located within a segment, a plurality of segments, a portion of/entire apical region, a portion of/entire mid-ventricular region, a portion of/entire basal region, entire surface of the LV or RV, or the like.

Next, the method assigns at least a portion of the map points from the set of map points into geometric areas. In some embodiments, the geometric area represents a triangular area, and the assigning operation includes assigning a select map point to one or more triangular areas when the select map point falls within distance limits of neighboring map points. Optionally, the geometric area may represent a non-triangular area, such as a square, rectangle or other multi-sided polygon. The geometric (e.g., triangular) areas may include overlapping and/or non-overlapping geometric (e.g., triangular) areas. When the geometric areas are assigned, the geometric areas include vertices corresponding to the map points. In some instances, at least a portion of the geometric areas may further include map points within an interior portion of the geometric areas.

At 606, the method 600 forms a triangulation area that includes a set of map points from the point cloud data that includes at least a select number of map points within the region of interest. The triangulation area corresponds to the region of interest. The triangulation area is defined by the set of map points within the region of interest. For example, the navigation system 120 may determine boundaries of the triangulation area based on positions of one or more of the select map points within the region of interest. The set of map points within the triangulation area may identify the map points to be used by the navigation system 120 to form one or more triangles as described at 608.

At 608, the method 600 uses a triangulation technique algorithm, such as a DeLaunay triangulation algorithm, to generate at least one triangle within the triangulation area formed from at least a portion of the set of map points. For example, the navigation system 120 may generate a set of overlapping and/or non-overlapping triangles, in relation to FIGS. 7-8 and 11-12, and/or select the largest triangle corresponding to the region of interest.

In some embodiments, the assigning operation may include utilizing a triangulation algorithm to build triangles that include the map points as vertices wherein no map points fall within more than one of the triangles.

Additionally or alternatively, the assigning operation may further comprise assigning, to the geometric areas, map points that are positioned outside of the region of interest. In some embodiments, the assigning operation includes forming candidate geometric regions within the at least one segment, identifying a one of the candidate geometric regions having a select area to constitute a select geometric area, and assigning map points within the select geometric area to the select geometric area. In some embodiments, the assigning operation comprises calculating areas for a plurality of the geometric areas and calculating a sum of areas of the plurality of the geometric areas. In some embodiments, the assigning operation may include determining centroids for a plurality of the geometric areas.

Optionally, the assigning operation may further comprise determining a plurality of candidate triangular area combinations. The triangular areas combinations may include overlapping triangular areas and/or non-overlapping triangular areas.

Figure 7:
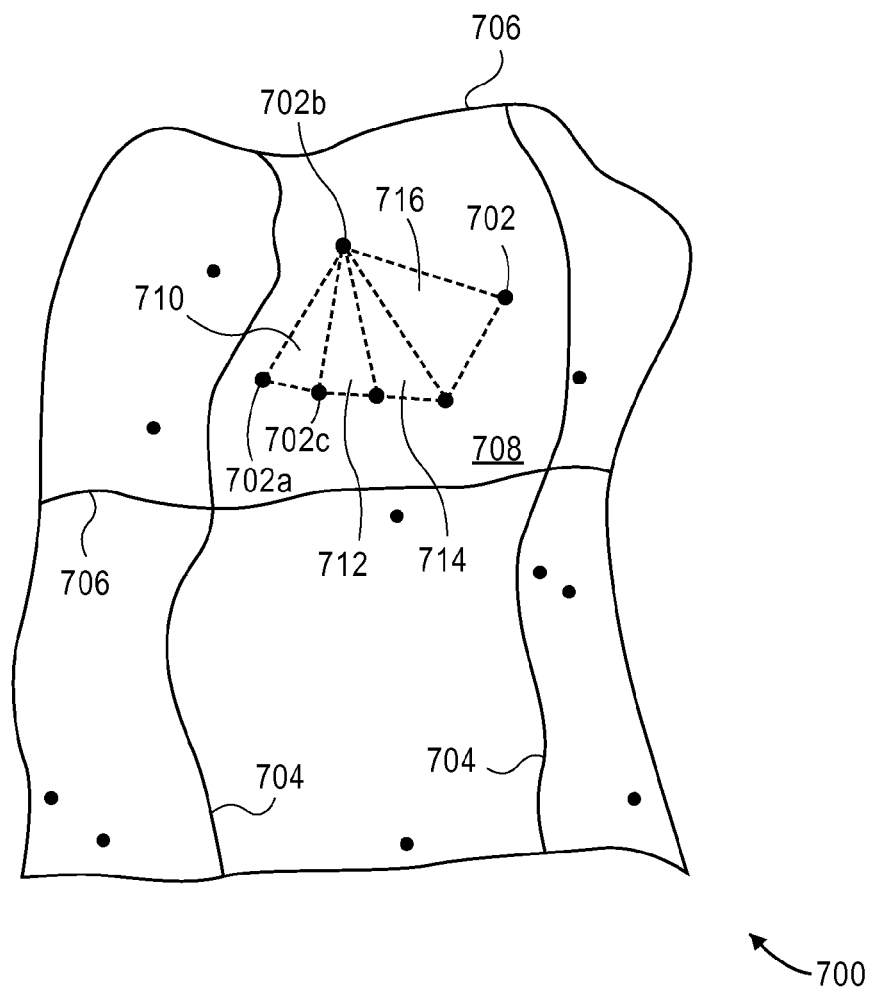
FIG. 7 illustrates a sub-divided region of interest within a three dimensional (3D) visualization of map points from a point cloud data set of the LV, in accordance with an embodiment disclosed herein.
Figure 8:
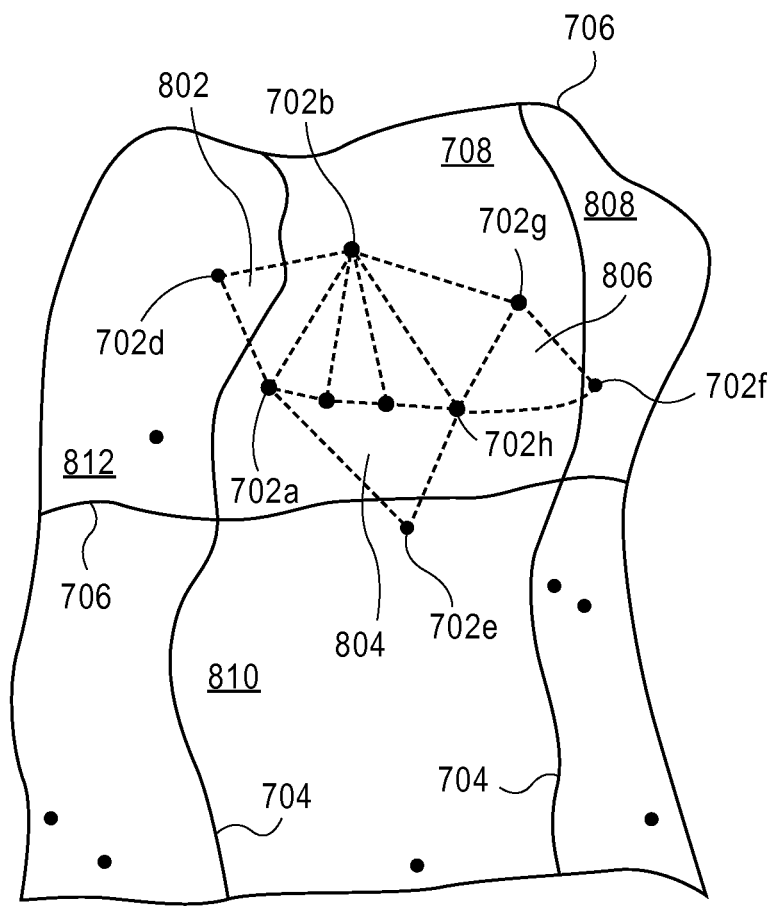
FIG. 8 illustrates a sub-divided region of interest within a three dimensional (3D) visualization of map points from a point cloud data set of the LV, in accordance with an embodiment disclosed herein.

FIGS. 7 and 8 illustrate a segment 708 selected as a region of interest within a three dimensional (3D) visualization 700 that may be displayed on display 158 of map points 702 from a point cloud data set of the LV. The segment 708 is bounded by circumferential segment boundaries 706 and longitudinal segment boundaries 704. It should be noted, although the region of interest is shown as the segment 708 in FIGS. 7 and 8, the region of interest may be within a segment, a plurality of segments, a portion of/entire apical region, a portion of/entire mid-ventricular region, a portion of/entire basal region, entire surface of the LV or RV, or the like.

The navigation system 120 may apply a triangulation technique algorithm (TTA) (e.g., DeLaunay triangulation algorithm) to generate non-overlapping triangles 710-716 within a triangulation area corresponding to the region of interest (e.g., the segment 708). By way of example, the TTA builds triangles such that no pint in the original map point data set is within a circumcircle of the resulting triangles. The TTA may maximize the minimum angle of the triangles to avoid skinny triangles. Each of the non-overlapping triangles 710-716 are formed from map points 702 within the segment 708. For example, the triangle 710 is formed from map points 702a-c. It should be noted that in embodiments, non-overlapping or overlapping triangles may be generated by the navigation system 120 using the TTA. The TTA may use map points in neighboring regions (beyond the region of interest but close to a perimeter of the region of interest). When map points are used from neighboring regions, the TTA apply one or more constraints to limit which map points may be used from the neighboring region. For example, the limit/constraint may represent a maximum number of map points that are located outside the region of interest may be used within any single triangle and/or used collectively within all of the triangles. Additionally or alternatively, the limit/constraint may represent a minimum number of map points that are within the region of interest that may be used within any single triangle and/or used collectively within all of the triangles.

Additionally or alternatively, non-overlapping triangles 802-806 may be formed using map points (e.g., 702e-f) of a triangulation area that is located entirely outside or partially extends outside the region of interest (e.g., the segment 708). FIG. 8 illustrates non-overlapping triangles 802-806 generated from map points 702-e-f within neighboring segments 808-812 that are not within the segment 708 or the region of interest. The number of map points (e.g., the map points 702e-f) or triangles (e.g., non-overlapping triangles 802-806) formed outside or within the region of interest (e.g., the segment 708) may be predetermined by the navigation system 120 or set by the clinician through the operator user interface 154. Optionally, the navigation system 120 may generate triangles with a predetermined minimum and/or maximum size.

For example, the clinician may instruct the navigation system 120, using the TTA, to have at least two map points of each non-overlapping triangle within the segment 708 (e.g., the region of interest). The navigation system 120 may generate three triangles 802-806 having map points 702e-f outside the segment 708 each with two map points 702a-b, 702a and 702h, and 702g-h, respectively, within the segment 708. It should be noted that in some embodiments, more (e.g., FIG. 7) or less (e.g., one map point) than two map points may be selected by the clinician and/or used by the navigation system 120.

Optionally, the navigation system 120 may limit the number of map points that may be located outside the region of interest or set the triangulation area to extend a predetermined distance beyond a border of the region of interest. For example, the clinician may instruct the navigation system 120 to exclude candidate triangles having vertices at map points that are located more than 1 millimeter beyond a border of the region of interest. It should be noted that in embodiments a distance of greater than or less than 1 millimeter may be selected.

Additionally or alternatively, the navigation system 120 may select a triangle from the candidate triangle(s) utilizing various criteria. For example, the navigation system 100 may select one or more triangles to be used when assessing motion specific map point data by choosing, from candidate triangles based on various criteria. For example, a subset of the candidate triangles may be selected where the subset of candidate triangles covers the greatest area or portion of the region of interest. The triangulation or geometric area designations process may begin by defining multiple candidate geometric areas (e.g. triangles), where the geometric areas may extend beyond borders of the region of interest. Constraints may be placed upon the extent to which map points outside of the region of interest may be utilized to define vertices of the geometric area. For example, a constraint may be placed on the geometric area defining a minimum size for the geometric area. Additionally or alternatively, the constraint may define how far beyond a border of the region of interest, map points may be chosen for use as vertices to define the geometric area(s). For example, a constraint may provide that when a map point is outside of the boundaries of the region of interest, the map point must be within a select distance of the boundary of the region of interest. Once one or more candidate triangles are defined, the process next selects one or more of the triangles to be utilized. For example, a largest triangle may be selected where the largest triangle includes all possible triangles between map points in the region of interest, and including map points beyond the boundary of the region of interest, but within a predetermined distance from the boundary of the region of interest. In the foregoing example, the candidate triangles may overlap one another. The area of each candidate triangle is determined and utilize to select one or more of the triangle to use in subsequent analysis of motion specific map point data. For example, the candidate triangle having the largest area may be chosen. Additionally or alternatively, the candidate triangle having a relatively large area (relative to other triangles) may be chosen when the candidate triangle has the fewest number of map points outside of the region of interest.

Additionally or alternatively, the navigation system (and method) may generate a large number of smaller candidate triangles that either overlap or do not overlap one another. The collection of smaller candidate triangles with substantially cover the region of interest and may extend beyond boundaries of the region of interest. Once the collection of smaller candidate triangles are determined, the process analyzes various possible combinations and permutations of the candidate triangles until identifying a combination of candidate triangles that satisfies a criteria of interest. For example, the criteria may correspond to an overall area that is substantially similar to the overall area of the region of interest and/or include a limited number of map points outside of the boundaries of the region of interest (e.g., a segment, heart wall, etc.).

As another example embodiment, the navigation system (and method) may venerate the candidate triangles by stepping through each map point and identifying at least two other map points that represent nearest or select neighbors to the present map point. The nearest/select neighbor map points may be positioned a distant from the present map point as defined by minimum and/or maximum distance constraints. The angular relation between the present map point and the select neighboring map points may also be used to determine which map points are potential candidates as the nearest/select neighbor map points. For example, the nearest neighbor map points may be selected to define a shape or the geometric area that has a select minimum angle between lines connecting the map points.

The system and methods may perform various analysis upon the map points. For example, for each present map point, a triangle is formed with the present map points to closest/select neighbor map points. The geometric shape (e.g. triangle) that is formed is representative of the mechanical behavior at the point within the geometric shape. For each map point, the areas of the geometric shapes that utilize the current map point as a vertices may be summed to obtain an area representative of the area around the present map point. As another example, a centroid for the geometric shape may be found and the area of the geometric shape encompassing the centroid may be representative of the centroid location. As an example, an equation for determining the centroid of a triangle may be:

$$(x,y,z)\text{centroid} = [(x1+x2+x3)/3, (y1+y2+y3)/3, (z1+z2+z3)/3],$$

where X1, Y1 represent the coordinates of one map point, X2,Y2 represent the coordinates of a second map point and X3,Y3 represent the coordinates of a third map point defining the triangular area.

Figure 10:
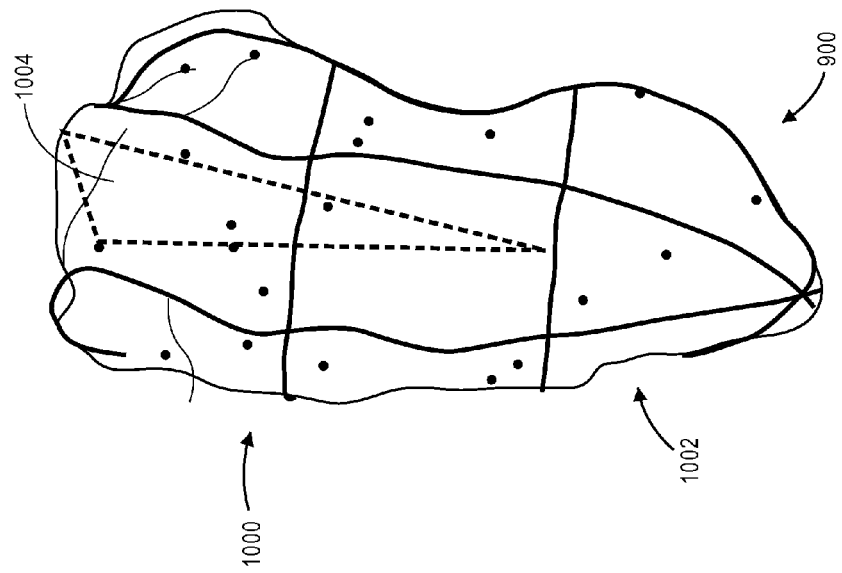
FIG. 10 illustrates a 3D visualization of a point cloud data set of the LV with a triangle corresponding to a region of interest, in accordance with an embodiment disclosed herein.
Figure 9:
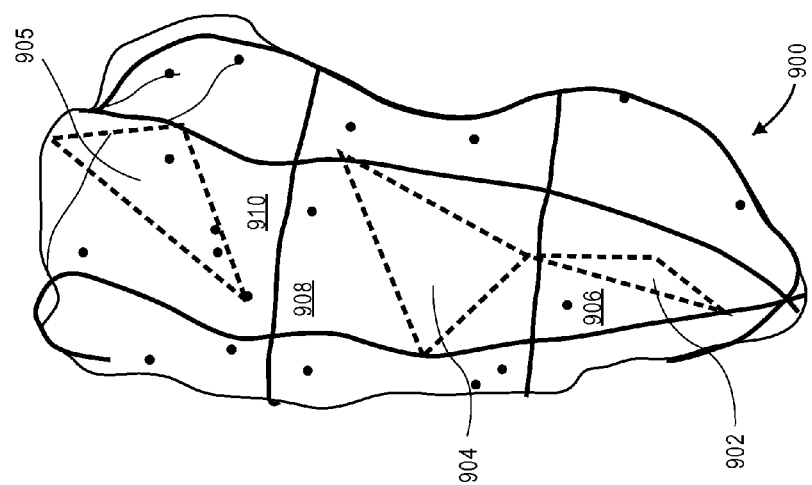
FIG. 9 illustrates a 3D visualization of a point cloud data set of the LV with a triangle corresponding to a region of interest, in accordance with an embodiment disclosed herein.

FIGS. 9 and 10 illustrate a 3D visualization 900 of a point cloud data set of the LV with a triangle corresponding to a region of interest selected by the navigation system 120 as the largest triangle by area that may be displayed on display 158. FIG. 9 illustrates three regions of interest, segments 906-910, each with triangles 902-905, respectively, selected as being the largest triangles by the navigation system 120 from all possible triangles using the TTA. FIG. 10 illustrates a region of interest that may be displayed on display 158, a wall portion 1000 (without the apical region 1002), with a triangle 1004, selected as being the largest triangle by the navigation system 120 from all possible triangles using the TTA.

Figure 11:
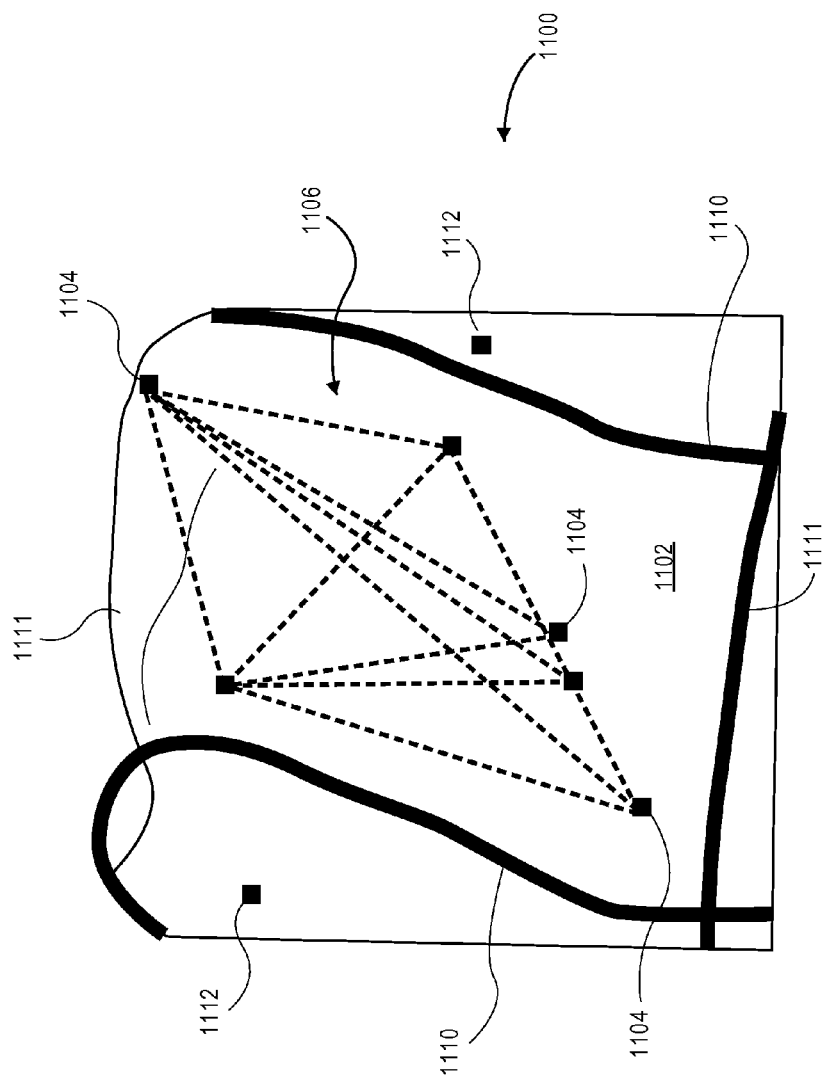
FIG. 11 illustrates a sub-divided region of interest within a three dimensional (3D) visualization of map points from a point cloud data set of the LV, in accordance with an embodiment disclosed herein.

Optionally, all generated triangles 1106 within the region of interest, overlapping or non-overlapping, by the navigation system 120 are combined or added together. FIG. 11 illustrate a segment 1102 selected as a region of interest within a three dimensional (3D) visualization 1100 of map points 1104 from a point cloud data set of the LV. The segment 1102 is bounded by circumferential segment boundaries 1111 and longitudinal segment boundaries 1110. The navigation system 120 generated, using the TTA, all possible triangles 1106 from map points 1104 within the segment 1102. It should be noted, that in some embodiments, map points 1112 outside the region of interest may be used to form triangles as described above.

Figure 12A:
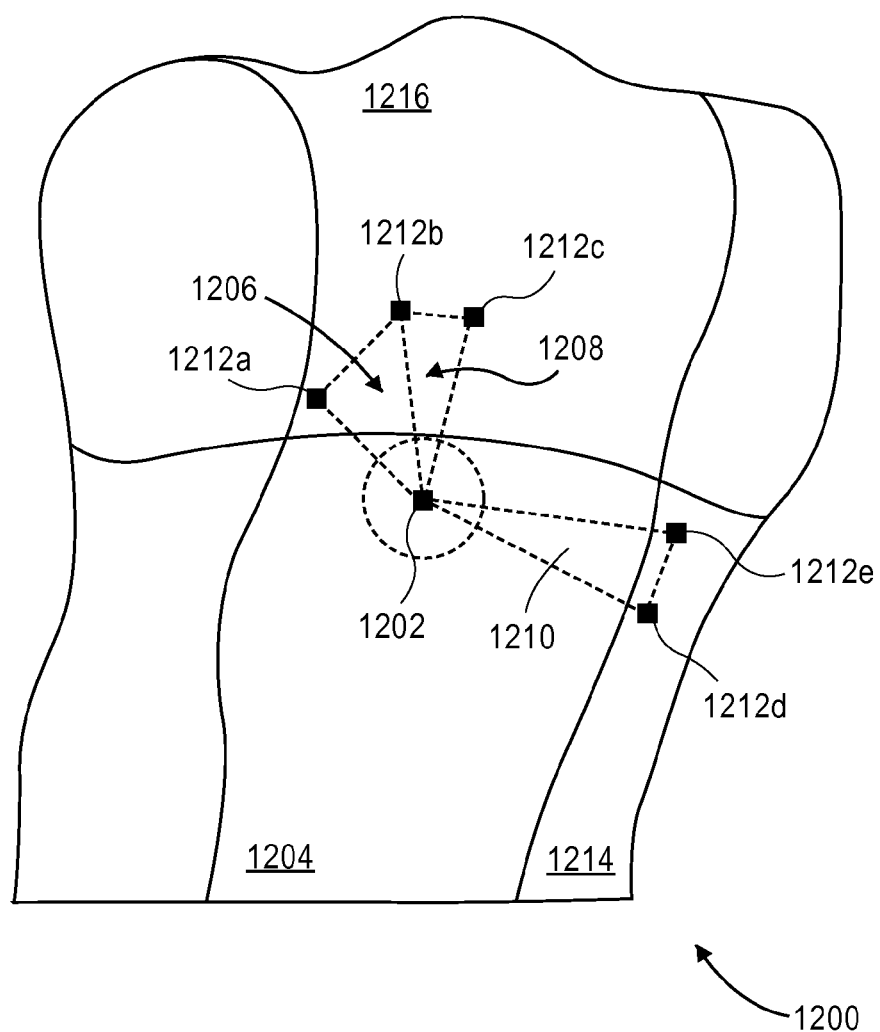
FIGS. 12a-b illustrate a map point within a region of interest of a three dimensional (3D) visualization from a point cloud data set of the LV.
Figure 12B:
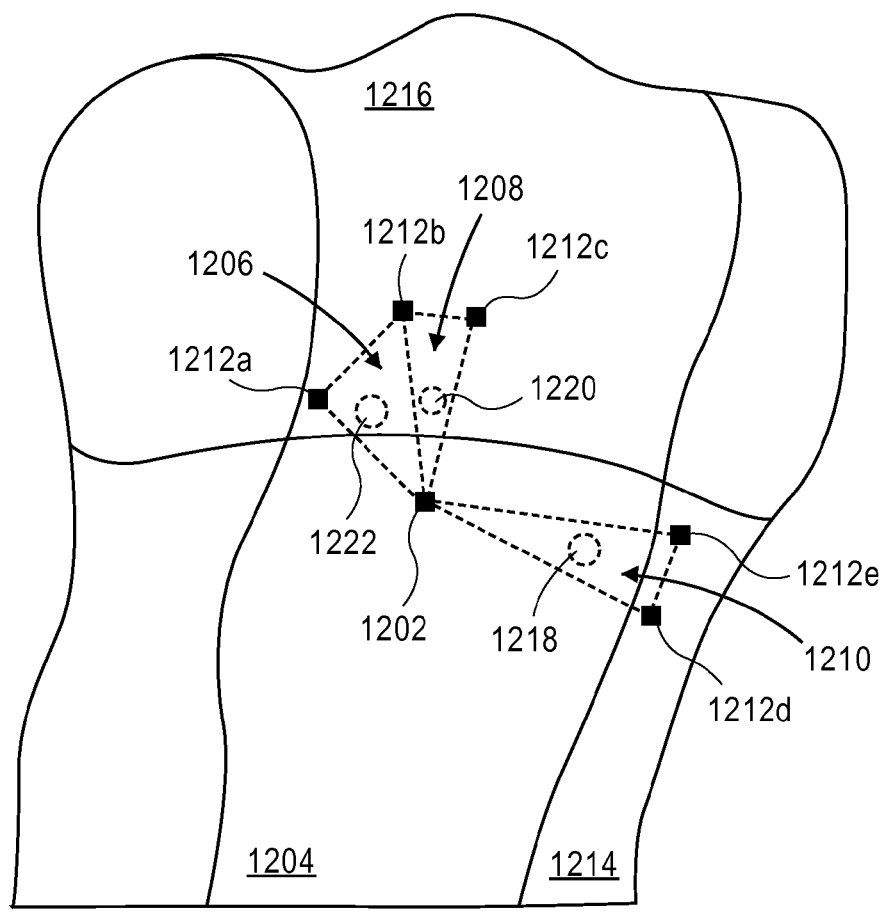

Additionally or alternatively, each of the map points are combined into one or more triangles with two neighboring points that satisfy a minimum and/or a maximum distance constraint. FIGS. 12a-b illustrates a map point 1202 within a segment 1204 (e.g., the region of interest) of a three dimensional (3D) visualization 1200 of map points 1202, 1212a-e from a point cloud data set of the LV that may be displayed on display 158. The map point 1202 is combined with map points 1212a-e of neighboring segments 1214-1216 to form three triangles 1206-1210. The navigation system 120 may determine from one or more of the triangles 1206-1210 the mechanical behavior of the map point 1202. Optionally, the navigation system 120 may determine from the sum or combined area of one or more of the triangles 1206-1210 the area around the map points 1202.

Additionally or alternatively, the navigation system 120 may determine centroids 1218-1222 for each triangle 1206-1210 using equation 1 below based on the Cartesian coordinates of the map points 1202, 1212a-e forming the triangle 1206-1210. For example, the Cartesian coordinates of the centroid 1222 for the triangle 1206 within the visualization 1200 will be positioned at the sum of the x, y, and z coordinate of the map points 1202, 1212a, and 1212b, separately, divided by three.

$$\text{centroid}(x, y, z,) = \left( \frac{x_1 + x_2 + x_3}{3}, \frac{y_1 + y_2 + y_3}{3}, \frac{z_1 + z_2 + z_3}{3} \right) \quad \text{(Equation 1)}$$

Figure 13:
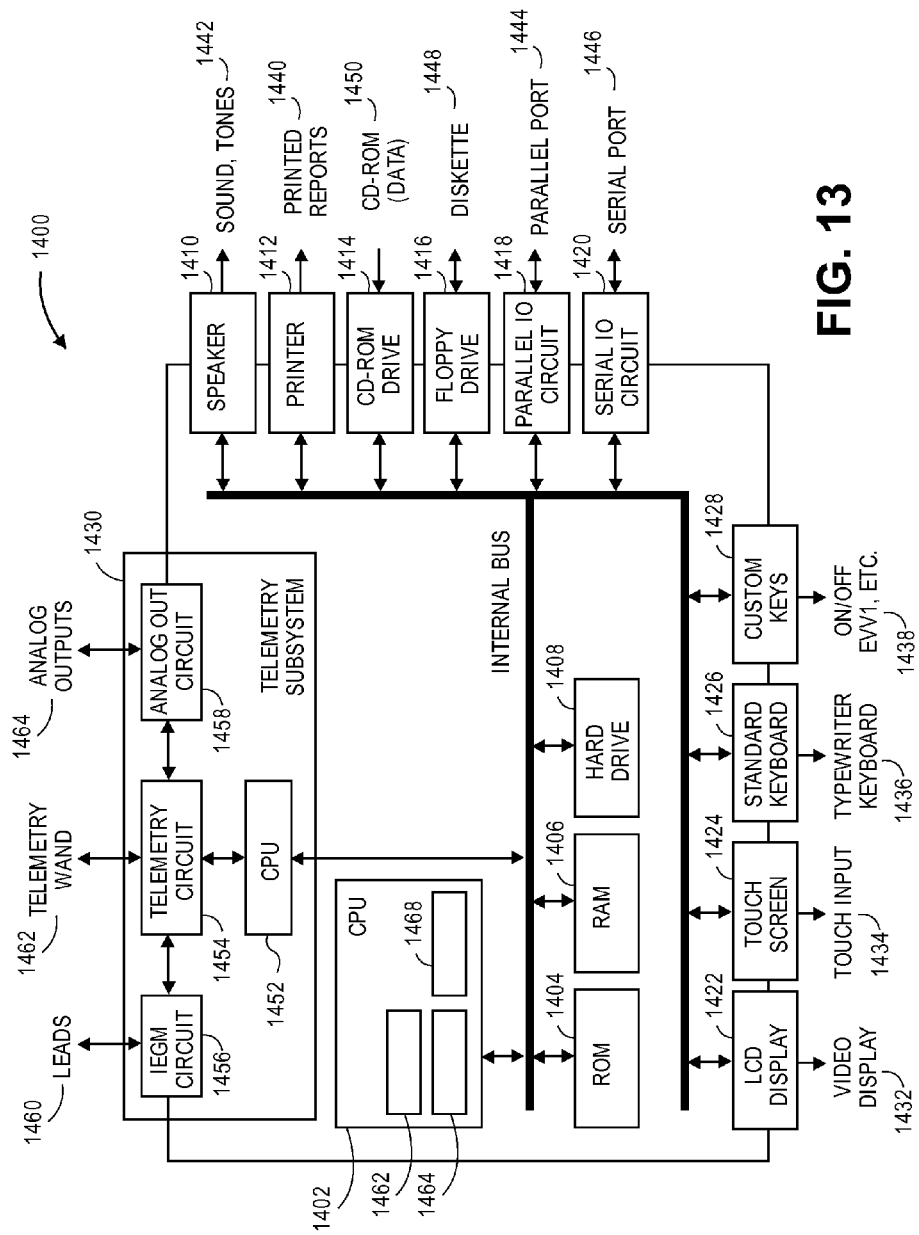
FIG. 13 illustrates a system for analyzing motion data in accordance with an embodiment.

FIG. 13 illustrates a functional block diagram of an embodiment of an electronic control unit (ECU) 1400 that is operated in accordance with the processes described herein to analyze motion data and to interface with the CNS 110. The ECU 1400 may be a workstation, a portable computer, a PDA, a cell phone and the like. The ECU 1400 includes an internal bus that connects/interfaces with a Central Processing Unit (CPU) 1402, ROM 1404, RAM 1406, a hard drive 1408, the speaker 1410, a printer 1412, a CD-ROM drive 1414, a floppy drive 1416, a parallel I/O circuit 1418, a serial I/O circuit 1420, the display 1422, a touch screen 1424, a standard keyboard connection 1426, custom keys 1428, and a telemetry subsystem 1430. The internal bus is an address/data bus that transfers information between the various components described herein. The hard drive 1408 may store operational programs as well as data, such as waveform templates and detection thresholds.

The CPU 1402 typically includes a microprocessor, a microcontroller, or equivalent control circuitry, and may interface with the CNS 110. The CPU 1402 may include RAM or ROM memory, logic and timing circuitry, state machine circuitry, and I/O circuitry to interface with the CNS 110. The display 1422 (e.g., may be connected to the video display 1432). The touch screen 1424 may display graphic information relating to the CNS 110. The display 1422 displays various information related to the processes described herein. The touch screen 1424 accepts a user's touch input 1434 when selections are made. The keyboard 1426 (e.g., a typewriter keyboard 1436) allows the user to enter data to the displayed fields, as well as interface with the telemetry subsystem 1430. Furthermore, custom keys 1428 turn on/off 1438 (e.g., EVVI) the ECU 1400. The printer 1412 prints copies of reports 1440 for a physician to review or to be placed in a patient file, and speaker 1410 provides an audible warning (e.g., sounds and tones 1442) to the user. The parallel I/O circuit 1418 interfaces with a parallel port 1444. The serial I/O circuit 1420 interfaces with a serial port 1446. The floppy drive 1416 accepts diskettes 1448. Optionally, the floppy drive 1416 may include a USB port or other interface capable of communicating with a USB device such as a memory stick. The CD-ROM drive 1414 accepts CD ROMs 1450.

The CPU 1402 is configured to analyze PS motion data collected by the CNS 110 for a plurality of map points to determine a point cloud data set of the map points stored on data storage (e.g., ROM 1404, RAM 1406, hard drive 1408). The data storage is configured to store map point data collected by an intravascular mapping tool configured to be inserted into at least one of the endocardial or epicardial space. The mapping tool is maneuvered to select locations proximate to surfaces of the heart, while collecting the map point data at map points to form a point cloud data set during at least one cardiac cycle. The map point data represents at least one of motion or electrical activity data at the map points.

The CPU 1402 includes a segmentation analysis circuit module 1464 that is configured to automatically assign segment identifiers (IDs), which are associated with segments of the heart separated by circumferential and longitudinal boundaries, to the map points based on a position of the map point from the point cloud data set. The CPU 1402 is further configured to select a region of interest from the point cloud data set, segment the region of interest into at least one segment that includes a corresponding set of map points from the point cloud data set, and assign at least a portion of the map points from the set of map points into geometric areas. In some embodiments, the processor 1402 assigns the map points utilizing a triangulation algorithm to build triangles that include the map points as vertices wherein no map points fall within more than one of the triangles. In some embodiments, the processor 1402 assigns, to the geometric areas, map points that are positioned outside of the region of interest. In some embodiments, the processor 1402 is further configured to form candidate geometric regions within the at least one segment, identify a one of the candidate geometric regions having a select area to constitute a select geometric area, and assign map points within the select geometric area to the select geometric area. In some embodiments, the processor 1402 may calculate areas for a plurality of the geometric areas and calculate a sum of areas of the plurality of the geometric areas. In some embodiments, the processor 1402 may determine centroids for a plurality of the geometric areas. In some embodiments, the processor 1402 is further configured assign a plurality of geometric areas to include vertices corresponding to the map points, at least a portion of the geometric areas further including map points within an interior portion of the geometric areas. In some embodiments, the processor 1402 is further configured assign, as the geometric areas, a plurality of candidate triangular area combinations, including overlapping triangular areas and non-overlapping triangular areas. The geometric area may represent a triangular area, and the processor 1402 assign a select map point to one or more triangular areas when the select map point falls within distance limits of neighboring map points.

The CPU 1402 also includes a position waveform generation circuit module 1462 that may generate position waveforms of selected reference locations based a coordinate system (e.g., Cartesian coordinate system, cylindrical coordinate system, or the like) as described herein. The CPU 1402 also includes a strain analysis circuit module 1468 that may determine the strain (e.g., linear or longitudinal strain, radial strain, circumferential strain), as explained herein.

The telemetry subsystem 1430 includes a central processing unit (CPU) 1452 in electrical communication with a telemetry circuit 1454, which communicates with both an IEGM circuit 1456 and an analog out circuit 1458. The circuit 1456 may be connected to leads 1460. The circuit 1456 may also be connected to implantable leads to receive and process IEGM cardiac signals. Optionally, the IEGM cardiac signals sensed by the leads may be collected by the CNS 110 and then transmitted, to the ECU 1400, wirelessly to the telemetry subsystem 1430 input.

The telemetry circuit 1454 is connected to a telemetry wand 1462. The analog out circuit 1458 includes communication circuits to communicate with analog outputs 1464. The ECU 1400 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 1400 to the CNS 110.

It should be noted that although the above embodiments may focus on strain calculations in the LV, it should be understood, by one in the art, that the above described techniques may also be applied to other chambers and other organs in which local biomechanical behavior is interest. Additionally, it should be noted that although the above embodiments may focus on longitudinal strain, it should be understood by one in the art that the above described techniques may also be applies to radial positioned from endocardial and epicardial map points across the myocardial wall to obtain radial strain which is indicative of wall thickening. Similarly, circumferential positions can be used to obtain a measure of active twist during contraction.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. A method for subdividing a region of interest, the method comprising:
   receiving point specific (PS) motion data from an intravascular mapping tool configured to be inserted into at least one of the endocardial or epicardial space, the mapping tool maneuvered to select locations against surfaces of the heart, while collecting PS motion data at map points to form a point cloud data set during at least one cardiac cycle, the PS motion data representing motion activity data at the map points; and
   utilizing one or more processors for:
      selecting a region of interest from the point cloud data set;
      segmenting the region of interest into at least one segment that includes a corresponding set of map points from the point cloud data set; and
      assigning the PS motion data for at least a portion of the map points from the set of map points into geometric areas; and
      determining a mechanical behavior for at least one of the geometric areas based on the PS motion data for the corresponding map points.

2. The method of claim 1, wherein the assigning operation includes utilizing a triangulation algorithm to build triangles that include the map points as vertices wherein no map points fall within more than one of the triangles, and to utilize the PS motion data at the vertices to calculate the mechanical behavior for the corresponding geometric areas.

3. The method of claim 1, wherein the assigning further comprises assigning, to the geometric areas, map points that are positioned outside of the region of interest.

4. The method of claim 1, wherein the assigning operation includes forming candidate geometric regions within the at least one segment, identifying a subset of the candidate geometric regions having a select area to constitute a select geometric area, and assigning map points within the select geometric area to the select geometric area.

5. The method of claim 4, further comprising calculating areas for a plurality of the geometric areas and calculating a sum of areas of the plurality of the geometric areas, and utilizing the sum to identify the subject of the candidate geometric regions that cover the greatest area.

6. The method of claim 1, further comprising determining centroids for a plurality of the geometric areas.

7. The method of claim 1, wherein a plurality of geometric areas include vertices corresponding to the map points, at least a portion of the geometric areas further including map points within an interior portion of the geometric areas.

8. The method of claim 1, wherein the assigning operation further comprises a plurality of candidate triangular area combinations, including overlapping triangular areas and non-overlapping triangular areas.

9. The method of claim 1, wherein the geometric area represents a triangular area, and the assigning operation includes assigning a select map point to one or more triangular areas when the select map point falls within distance limits of neighboring map points.

10. A system comprising:
    an intravascular mapping tool configured to collect point specific (PS) motion data when inserted into at least one of the endocardial or epicardial space, the mapping tool configured to be maneuvered to select locations against surfaces of the heart, while collecting the PS motion data at map points to form a point cloud data set during at least one cardiac cycle, the PS motion data representing motion activity data at the map points; and
    a processor configured to:
       select a region of interest from the point cloud data set;
       segment the region of interest into at least one segment that includes a corresponding set of map points from the point cloud data set;
       assign the PS motion data for at least a portion of the map points from the set of map points into geometric areas; and
       determine a mechanical behavior for at least one of the geometric areas based on the PS motion data for the corresponding map points.

11. The system of claim 10, wherein the processor is further configured to assign the map points utilizing a triangulation algorithm to build triangles that include the map points as vertices wherein no map points fall within more than one of the triangles, and to utilize the PS motion data at the vertices to calculate the mechanical behavior for the corresponding geometric areas.

12. The system of claim 10, wherein the processor is further configured to assign, to the geometric areas, map points that are positioned outside of the region of interest.

13. The system of claim 10, wherein the processor is further configured to form candidate geometric regions within the at least one segment, identify a subset of the candidate geometric regions that cover a greatest area of the region of interest to constitute a select geometric area, and assign map points within the select geometric area to the select geometric area.

14. The system of claim 13, wherein the processor is further configured to calculate areas for a plurality of the geometric areas and calculate a sum of areas of the plurality of the geometric areas, the processor utilizing the sum to identify the subject of the candidate geometric regions that cover the greatest area.

15. The system of claim 10, wherein the processor is further configured to determine centroids for a plurality of the geometric areas.

16. The system of claim 10, wherein the processor is further configured to assign a plurality of geometric areas to include vertices corresponding to the map points, at least a portion of the geometric areas further including map points within an interior portion of the geometric areas.

17. The system of claim 10, wherein the processor is further configured to assign, as the geometric areas, a plurality of candidate triangular area combinations, including overlapping triangular areas and non-overlapping triangular areas.

18. The system of claim 10, wherein the geometric area represents a triangular area, and the processor assigns a select map point to one or more triangular areas when the select map point falls within distance limits of neighboring map points.

19. The system of claim 10, a display configured to display the assigned map points.

20. The system of claim 10, wherein the mechanical behavior corresponds to strain.

\* \* \* \* \*